US010182807B2

(12) United States Patent
Bridgeman et al.

(10) Patent No.: US 10,182,807 B2
(45) Date of Patent: Jan. 22, 2019

(54) SUTURE ANCHOR APPARATUS

(71) Applicant: Nuvectra Corporation, Plano, TX (US)

(72) Inventors: Elliot Bridgeman, Big Lake, MN (US); Lawrence Kane, St. Paul, MN (US)

(73) Assignee: Nuvectra Corporation, Plano, TX (US)

( * ) Notice: Subject to any disclaimer, the term of this patent is extended or adjusted under 35 U.S.C. 154(b) by 656 days.

(21) Appl. No.: 14/445,382

(22) Filed: Jul. 29, 2014

(65) Prior Publication Data

US 2015/0039028 A1 Feb. 5, 2015

Related U.S. Application Data

(60) Provisional application No. 61/860,291, filed on Jul. 31, 2013.

(51) Int. Cl.
*A61B 17/04* (2006.01)
*A61N 1/05* (2006.01)

(52) U.S. Cl.
CPC .......... *A61B 17/0401* (2013.01); *A61N 1/059* (2013.01); *A61B 2017/0445* (2013.01); *A61B 2017/0459* (2013.01); *A61B 2017/0464* (2013.01); *A61N 2001/0582* (2013.01)

(58) Field of Classification Search
CPC ............ A61B 17/0401; A61B 17/0487; A61B 2017/0406; A61B 2017/0408; A61B 2017/0404; A61B 2017/042; A61B 2017/0422; A61B 2017/0432; A61B 2017/0441; A61B 2017/0443; A61B 2017/0445; A61B 2017/0446; A61B 2017/045; A61B 2017/0454; A61B 2017/0459; A61B 2017/0462; A61B 2017/0448; A61B 2017/0417; A61B 2017/0451; A61B 2017/0456; A61B 2017/0458; A61B 2017/0488; A61B 2017/0464; A61N 1/059; A61N 1/0558; A61N 1/057; A61N 1/058; A61N 1/0539; A61N 1/05; A61N 2001/0582

See application file for complete search history.

(56) References Cited

U.S. PATENT DOCUMENTS

| | | | | |
|---|---|---|---|---|
| 5,674,273 A * | 10/1997 | Helland | ............. | A61N 1/05 604/175 |
| 7,082,337 B2 * | 7/2006 | Sommer | ............. | A61N 1/057 604/175 |
| 2007/0276437 A1 * | 11/2007 | Call | ............. | A61B 17/0487 606/232 |
| 2009/0125061 A1 * | 5/2009 | Rivard | ............. | A61N 1/057 606/232 |
| 2009/0248071 A1 * | 10/2009 | Saint | ............. | A61B 17/0401 606/232 |

(Continued)

FOREIGN PATENT DOCUMENTS

WO  WO 2006116454 A2 * 11/2006 ............. A61N 1/056

*Primary Examiner* — Robert Lynch
(74) *Attorney, Agent, or Firm* — Haynes and Boone, LLP; Eric Q. Li (57) ABSTRACT

In various examples, a suture anchor includes a sheath including a lumen. A frame member is disposed at least partially within the sheath. The frame member includes at least two suture loops extending from the sheath. The suture loops are configured to receive a suture, wherein tightening of the suture causes compression of the frame member to constrict the lumen of the sheath.

21 Claims, 4 Drawing Sheets

(56) References Cited

U.S. PATENT DOCUMENTS

2011/0009935 A1\* 1/2011 Kane .................. A61N 1/057
607/116
2011/0178573 A1\* 7/2011 Nguyen-Stella ..... A61N 1/0558
607/46

\* cited by examiner

SUTURE ANCHOR APPARATUS

CROSS REFERENCE TO RELATED APPLICATIONS

This application claims the benefit of priority to U.S. Provisional Application Ser. No. 61/860,291, filed on Jul. 31, 2013, entitled "SUTURE ANCHOR APPARATUS," which is incorporated by reference herein in its entirety.

BACKGROUND

The present invention relates to a suture anchor, and more specifically relates to a suture anchor for anchoring a lead.

Suture anchors often require that a suture be tied in direct contact with the material (often silicone or another similar material) forming the suture anchor and around the suture anchor in order to secure the suture anchor around a lead and, in turn, secure the lead in place with respect to a patient. However, tying sutures in direct contact with silicone (or another similar material) can create various risks due to different physicians tying sutures with varying degrees of force. Such risks include cutting through the silicone or other material of the suture anchor with the suture (if too much force is used in tying the suture) or improper securing of the lead (if too little force is used in tying the suture). Because of the inability to control the force with which a physician ties the suture around the suture anchor, there is a relatively high risk of failure of the suture anchor, for instance, because too much force or too little force was used in tying the suture around the suture anchor.

OVERVIEW

This overview is intended to provide an overview of subject matter of the present patent document. It is not intended to provide an exclusive or exhaustive explanation of the invention. The detailed description is included to provide further information about the present patent document.

The present inventors have recognized, among other things, that the subject matter can be used to anchor a therapy delivery element or other device with respect to a patient without a suture being directly in contact with a sheath of the suture anchor to decrease the likelihood of a suture cutting through an exterior of a suture anchor, as can be a problem with other suture anchors. The present inventors have further recognized, among other things, that the subject matter can be used to provide a suture anchor including a pre-loaded suture, thereby decreasing the amount of time required to engage the suture anchor by eliminating the need to put the suture in place first before tightening the suture. To better illustrate the apparatuses, systems, and methods described herein, a non-limiting list of examples is provided here:

Example 1 can include subject matter that can include a suture anchor including a sheath including a lumen. A frame member is disposed at least partially within the sheath. The frame member includes at least two suture loops extending from the sheath. The suture loops are configured to receive a suture, wherein tightening of the suture causes compression of the frame member to constrict the lumen of the sheath.

In Example 2, the subject matter of Example 1 is optionally configured such that the frame member includes a substantially circular shape when viewed from an end, the frame member being substantially coaxial with the lumen of the sheath.

In Example 3, the subject matter of Example 2 is optionally configured such that the frame member includes a wave-like pattern when flattened. The wave-like pattern includes peaks. The peaks form the suture loops with the frame member formed into the substantially circular shape.

In Example 4, the subject matter of any one of Examples 1-3 is optionally configured such that the frame member includes a wire form.

In Example 5, the subject matter of any one of Examples 1-4 is optionally configured such that the at least two suture loops extend from the sheath and are disposed substantially along a longitudinal line along an outer surface of the sheath.

In Example 6, the subject matter of any one of Examples 1-5 is optionally configured such that the frame member includes more than two suture loops.

In Example 7, the subject matter of any one of Examples 1-6 is optionally configured such that at least a portion of the sheath is laminated over the frame member.

In Example 8, the subject matter of any one of Examples 1-7 is optionally configured such that at least a portion of the sheath is overmolded with the frame member.

In Example 9, the subject matter of any one of Examples 1-8 is optionally configured such that the sheath includes a first portion and a second portion, wherein the first portion includes a first characteristic and the second portion includes a second characteristic different from the first characteristic.

In Example 10, the subject matter of any one of Examples 1-9 is optionally configured such that the lumen is sized to accept a therapy delivery element within the lumen, wherein the tightening of the suture constricts the lumen of the sheath to frictionally engage the therapy delivery element.

Example 11 can include, or can optionally be combined with any one of Examples 1-10 to include subject matter that can include a suture anchor including a sheath including a lumen. A frame member is disposed at least partially within the sheath. The frame member includes a wave-like pattern when flattened. The frame member includes at least two suture loops extending from the sheath. The suture loops are formed from peaks of the wave-like pattern of the frame member with the frame member formed into a substantially circular shape. The suture loops are configured to receive a suture, wherein tightening of the suture causes compression of the frame member to constrict the lumen of the sheath.

In Example 12, the subject matter of Example 11 is optionally configured such that the frame member includes a wire form.

In Example 13, the subject matter of any one of Examples 11-12 is optionally configured such that the at least two suture loops extend from the sheath and are disposed substantially along a longitudinal line along an outer surface of the sheath.

In Example 14, the subject matter of any one of Examples 11-13 is optionally configured such that at least a portion of the sheath is laminated over the frame member.

In Example 15, the subject matter of any one of Examples 11-14 is optionally configured such that at least a portion of the sheath is overmolded with the frame member.

In Example 16, the subject matter of any one of Examples 11-15 is optionally configured such that the sheath includes a first portion and a second portion, wherein the first portion includes a first characteristic and the second portion includes a second characteristic different from the first characteristic.

In Example 17, the subject matter of any one of Examples 11-16 is optionally configured such that the lumen is sized to accept a therapy delivery element within the lumen, wherein the tightening of the suture constricts the lumen of the sheath to frictionally engage the therapy delivery element.

Example 18 can include, or can optionally be combined with any one of Examples 1-17 to include subject matter that can include a suture anchor including a sheath including a lumen. The lumen is sized to accept a therapy delivery element within the lumen. A frame member is disposed at least partially within the sheath. The frame member includes a wave-like pattern when flattened. The frame member includes at least two suture loops extending from the sheath. The suture loops are formed from peaks of the wave-like pattern of the frame member with the frame member formed into a substantially circular shape. The suture loops are configured to receive a suture. The at least two suture loops extend from the sheath and are disposed substantially along a longitudinal line along an outer surface of the sheath, wherein tightening of the suture causes compression of the frame member to constrict the lumen of the sheath to frictionally engage the therapy delivery element.

In Example 19, the subject matter of Example 18 is optionally configured such that at least a portion of the sheath is laminated over the frame member.

In Example 20, the subject matter of any one of Examples 18-19 is optionally configured such that at least a portion of the sheath is overmolded with the frame member.

DETAILED DESCRIPTION

The present patent application relates to suture anchors. In various examples, as described herein, the suture anchors are configured to allow tightening of the suture anchor without direct contact of a suture with a sheath of the suture anchor. The suture anchors, in some examples, can be used to anchor various devices with respect to a patient, including, but not limited to, therapy delivery elements. In some examples, the therapy delivery element includes a fluid delivery conduit, such as a catheter, including an inner lumen that is placed to deliver a fluid, such as pharmaceutical agents, insulin, pain relieving agents, gene therapy agents, or the like from a fluid delivery device (e.g., a fluid reservoir and/or pump) to a respective target tissue site in a patient. In some examples, the therapy delivery element includes an electrical lead including a pacing or defibrillation lead, a stimulation lead, or a sensing lead.

Figure 1:
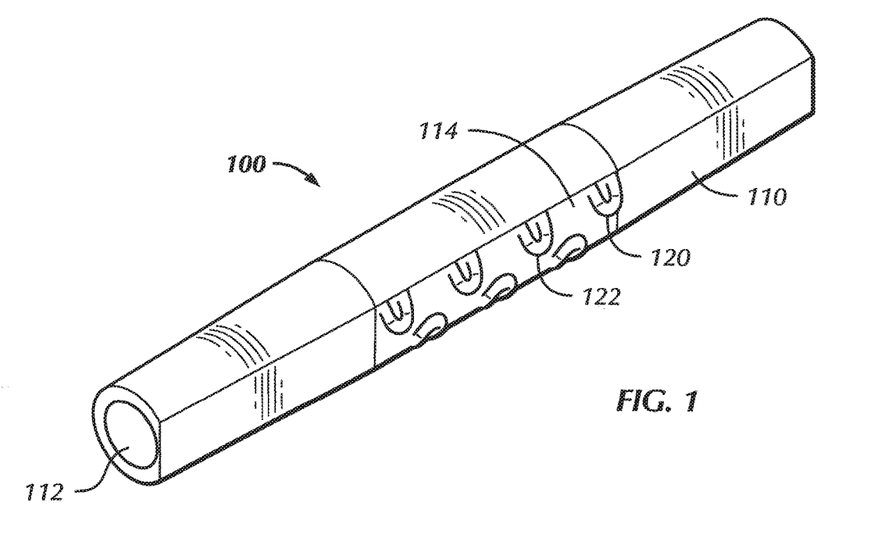
FIG. 1 is a perspective view of a suture anchor apparatus in accordance with at least one example of the invention.

Referring to FIG. 1, in some examples, a suture anchor 100 includes a sheath 110 including a lumen 112. In some examples, the sheath 110 is substantially tubular. In some examples, the sheath 110 is formed from silicone. In other examples, the sheath 110 can be formed from one or more materials other than or in addition to silicone. The lumen 112, in some examples, is disposed through the sheath 110 and is configured to accept a therapy delivery element within the lumen 112.

In some examples, the suture anchor 100 includes a frame member 120 disposed at least partially within the sheath 110. In some examples, the frame member 120 includes at least two suture loops 122 extending from the sheath 110. The suture loops 122, in some examples, are configured to receive a suture, wherein tightening of the suture causes compression of the frame member 120 to constrict the lumen 112 of the sheath 110. In some examples, the suture anchor 100 includes more than two suture loops 122. For instance, as shown in FIG. 1, the suture anchor 100 includes seven suture loops 122. In some examples, the suture is threaded through or otherwise placed within at least some of the suture loops 122. In some examples, one or more of the suture loops 122 can be used to anchor the suture anchor 100 to a patient. For example, a suture, staple, or other fastening device can be coupled between at least one of the suture loops 122 and the patient in order to secure the suture anchor 100 to the patient. In some examples, the one or more suture loops 122 used for securing the suture anchor 100 to the patient can be flared outwardly from the sheath 110 to facilitate securing of the suture anchor 100 to the patient.

In some examples, the sheath 110 includes a flattened or planar area 114 disposed at least around the suture loops 122. The flattened area 114, in some examples, provides for clearance between the suture loops 122 and the sheath 110 to facilitate threading of the suture through the suture loops 122 or tightening of the suture. The flattened area 114, in some examples, also allows for a decreased amount of material disposed between the suture loops 122 to facilitate tightening of the suture, compression of the frame member 120, and constriction of the lumen 112 of the sheath 110.

Figures 2A, 2B, 2C:
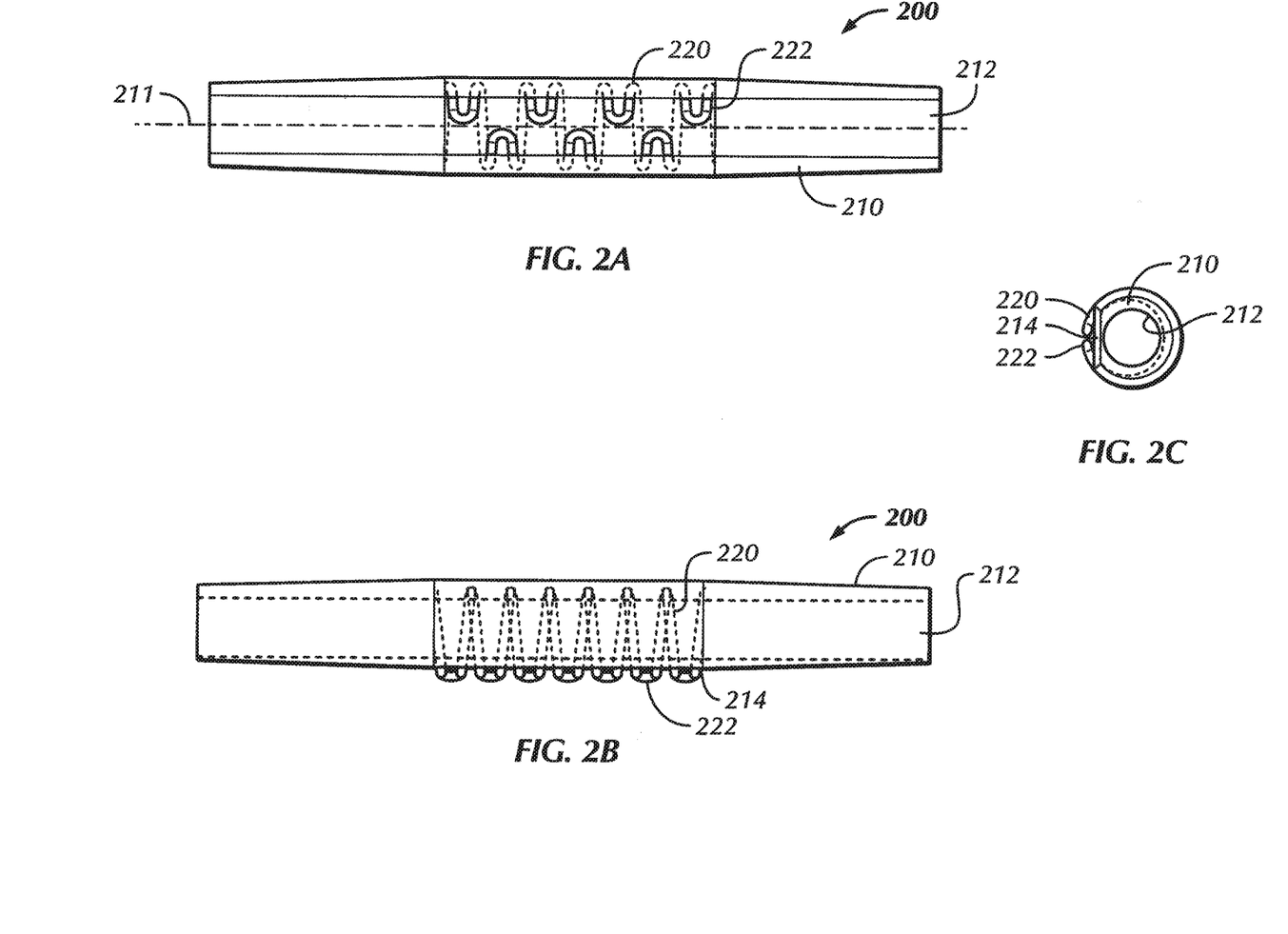
FIG. 2A is a top view of a suture anchor apparatus in accordance with at least one example of the invention.
FIG. 2B is a side view of a suture anchor apparatus in accordance with at least one example of the invention.
FIG. 2C is an end view of a suture anchor apparatus in accordance with at least one example of the invention.

Referring to FIGS. 2A-2C, in some examples, a suture anchor 200 includes a sheath 210 including a lumen 212. In some examples, the sheath 210 is formed from silicone. In other examples, the sheath 210 can be formed from one or more materials other than silicone. The lumen 212, in some examples, is disposed through the sheath 210 and is configured to accept a therapy delivery element within the lumen 212.

In some examples, the suture anchor 200 includes a frame member 220 disposed at least partially within the sheath 210. In some examples, the frame member 220 substantially forms a tubular shape disposed around the lumen 212 of the sheath 210. In some examples, the frame member 220 includes at least two suture loops 222 extending from the sheath 210. The suture loops 222, in some examples, are configured to receive a suture, wherein tightening of the suture causes compression of the frame member 220 to constrict the lumen 212 of the sheath 210. The at least two suture loops 222, in some examples, extend from the sheath 210 and are disposed substantially along a longitudinal line 211 along an outer surface of the sheath 210. In some examples, the suture anchor 200 includes more than two suture loops 222. For instance, as shown in FIG. 2A, the suture anchor 200 includes seven suture loops 222. In some examples, the suture is threaded through or otherwise placed within at least some of the suture loops 222. In some examples, one or more of the suture loops 222 can be used to anchor the suture anchor 200 to a patient. For example, a suture, staple, or other fastening device can be coupled between at least one of the suture loops 222 and the patient in order to secure the suture anchor 200 to the patient. In some examples, the one or more suture loops 222 used for securing the suture anchor 200 to the patient can be flared outwardly to facilitate securing of the suture anchor 200 to the patient. In some examples, the lumen 212 is sized to accept a therapy delivery element within the lumen 212, wherein the tightening of the suture constricts the lumen 212 of the sheath 210 to frictionally engage the therapy delivery element.

In some examples, the frame member 220 includes a substantially circular shape when viewed from an end, as seen in FIG. 2C. In some examples, the frame member 220 is substantially coaxial with the lumen 212 of the sheath 210.

In some examples, the frame member 220 includes a wave-like pattern when flattened, the wave-like pattern including peaks, the peaks forming the suture loops 222 with the frame member 220 formed into the substantially circular shape when viewed from an end. The wave-like pattern can take different forms in various examples, such as, for instance, a substantially sinusoidal wave pattern, a substantially triangular or saw-tooth wave pattern, a substantially square wave pattern, or the like, or a combination of two or more wave patterns. In some examples, the frame member 220 includes a wire form. In some examples, the wire form of the frame member 220 is drawn or extruded into wire and then formed into the pattern of the frame member 220, for instance, formed into the wavelike pattern and then further formed into the circular shape when viewed from the end. In some examples, the frame member 220 can be cut from stock. For instance, in some examples, the frame member 220 can be laser cut from a sheet of material and then formed into a substantially tubular (or other) form for use within the suture anchor 200. In further examples, other ways of manufacturing the frame member 220 are contemplated.

In some examples, the sheath 210 includes a flattened or planar area 214 disposed at least around the suture loops 222. The flattened area 214, in some examples, provides for clearance between the suture loops 222 and the sheath 210 to facilitate threading of the suture through the suture loops 222 or tightening of the suture. The flattened area 214, in some examples, also allows for a decreased amount of material disposed between the suture loops 222 to facilitate tightening of the suture, compression of the frame member 220, and constriction of the lumen 212 of the sheath 210.

In some examples, the sheath 210 is formed around the frame member 220. In some examples, at least a portion of the sheath 210 is overmolded with the frame member 220. The frame member 220, in some examples, is disposed partially within the sheath 210. The sheath 210, in various examples, is formed from at least one material including, but not limited to silicone. In some examples, the sheath 210 is formed from more than one material. In further examples, the sheath 210 is formed from a first material overmolded with the frame member 220 and then a second material, different from the first material, overmolded with the first material and/or the frame member 220. In some examples, the first material of the sheath 210 includes a first characteristic and the second material of the sheath 210 includes a second characteristic different from the first characteristic. Various characteristics are contemplated herein, such as, but not limited to, hardness, density, lubriciousness, resilience, elasticity, biocompatibility, color, or the like. The first and second materials can have one or more common characteristics and/or one or more differing characteristics. In some examples, the first material can include a hardness of a first durometer, and the second material can include a hardness of a second durometer higher or lower than the first durometer. In some examples, the first material includes a lower durometer to facilitate the sheath 210 constricting around and frictionally engaging the therapy delivery element, and the second material includes a higher durometer to provide a harder, more durable outer layer of the sheath 210. In other examples, different configurations are contemplated.

Figure 3A:
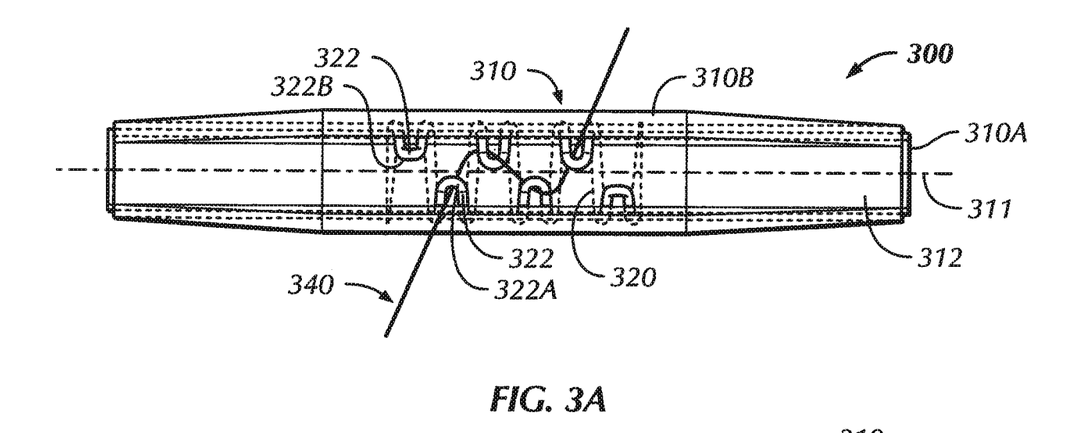
FIG. 3A is a top view of a suture anchor apparatus in accordance with at least one example of the invention.
Figure 3B:
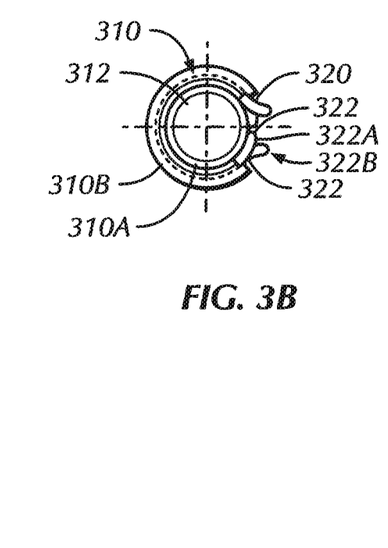
FIG. 3B is an end view of a suture anchor apparatus in accordance with at least one example of the invention.

Referring to FIGS. 3A and 3B, in some examples, a suture anchor 300 includes a sheath 310 including a lumen 312. In some examples, the sheath 310 is formed from silicone. In other examples, the sheath 310 can be formed from one or more materials other than silicone. The lumen 312, in some examples, is disposed through the sheath 310 and is configured to accept a therapy delivery element within the lumen 312.

In some examples, the suture anchor 300 includes a frame member 320 disposed at least partially within the sheath 310. In some examples, the frame member 320 substantially forms a tubular shape disposed around the lumen 312 of the sheath 310. In some examples, the frame member 320 includes at least two suture loops 322 extending from the sheath 210. The suture loops 322, in some examples, are configured to receive a suture 340, wherein tightening of the suture 340 causes compression of the frame member 320 to constrict the lumen 312 of the sheath 310. The at least two suture loops 322, in some examples, extend from the sheath 310 and are disposed substantially along a longitudinal line 311 along an outer surface of the sheath 310. In some examples, the suture anchor 300 includes more than two suture loops 322. For instance, as shown in FIG. 3A, the suture anchor 300 includes six suture loops 322. In some examples, the suture is threaded through or otherwise placed within at least some of the suture loops 322A. In some examples, one or more of the suture loops 322B can be used to anchor the suture anchor 300 to a patient. For example, a suture, staple, or other fastening device can be coupled between at least one of the suture loops 322 and the patient in order to secure the suture anchor 300 to the patient. In some examples, the suture loops 322B can be used to thread the suture 340 through the suture loops 322B as well as to secure the suture anchor 300 to the patient. In some examples, the one or more suture loops 322B used for securing the suture anchor 300 to the patient can be flared outwardly to facilitate securing of the suture anchor 300 to the patient. In some examples, the lumen 312 is sized to accept a therapy delivery element within the lumen 312, wherein tightening the suture 340 constricts the lumen 312 of the sheath 310 to frictionally engage the therapy delivery element.

In some examples, the frame member 320 includes a substantially circular shape when viewed from an end, as seen in FIG. 3B. In some examples, the frame member 320 is substantially coaxial with the lumen 312 of the sheath 310.

In some examples, the frame member 320 includes a wave-like pattern when flattened, the wave-like pattern including peaks, the peaks forming the suture loops 322 with the frame member 320 formed into the substantially circular shape when viewed from an end. The wave-like pattern can take different forms in various examples, such as, for instance, a substantially sinusoidal wave pattern, a substantially triangular or saw-tooth wave pattern, a substantially square wave pattern, or the like, or a combination of two or more wave patterns. In some examples, the frame member 320 includes a wire form. In some examples, the wire form of the frame member 320 is drawn or extruded into wire and then formed into the pattern of the frame member 320, for instance, formed into the wavelike pattern and then further formed into the circular shape when viewed from the end. In some examples, the frame member 320 can be cut from stock. For instance, in some examples, the frame member 320 can be laser cut from a sheet of material and then formed into a substantially tubular (or other) form for use within the suture anchor 300. In further examples, other ways of manufacturing the frame member 320 are contemplated.

In some examples, the sheath 310 is formed around the frame member 320. In some examples, at least a portion of the sheath 310 is laminated with the frame member 320. In some examples, a first portion 310A of the sheath 310 is laminated or otherwise disposed within the frame member 320. In some examples, a second portion 310B of the sheath 310 is laminated or otherwise disposed around the frame member 320. In some examples, the sheath 310 includes more or less than two portions 310A, 310B. In some examples, the first portion 310A is formed from a different material than the second portion 310B. The frame member 320, in some examples, is disposed partially within the sheath 310. For instance, in some examples, the frame member 320 is disposed between the first portion 310A and the second portion 310B. The sheath 310, in various examples, is formed from at least one material including, but not limited to silicone. In some examples, the sheath 310 is formed from more than one material. In further examples, the first portion 310A of the sheath 310 is formed from a first material and the second portion 310B of the sheath 310 is formed from a second material, different from the first material. In some examples, the first portion 310A of the sheath 310 includes a first characteristic and the second portion 310B of the sheath 310 includes a second characteristic different from the first characteristic. Various characteristics are contemplated herein, such as, but not limited to, hardness, density, lubriciousness, resilience, elasticity, biocompatibility, color, or the like. The first and second portions can have one or more common characteristics and/or one or more differing characteristics. In some examples, the first portion 310A can include a hardness of a first durometer, and the second portion 310B can include a hardness of a second durometer higher or lower than the first durometer. In some examples, the first portion 310A includes a lower durometer to facilitate the sheath 310 constricting around and frictionally engaging the therapy delivery element, and the second portion 310B includes a higher durometer to provide a harder, more durable outer layer of the sheath 310. In other examples, different configurations are contemplated.

Figure 4A:
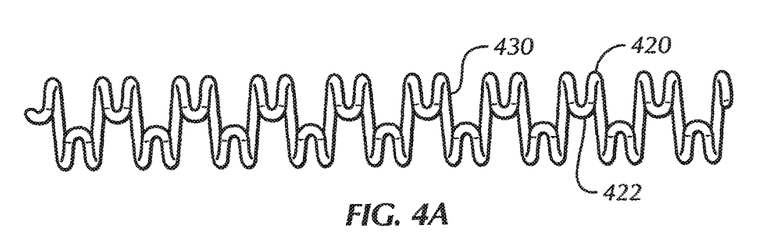
FIG. 4A is a top view of a frame member for use in a suture anchor apparatus in accordance with at least one example of the invention.
Figure 4B:
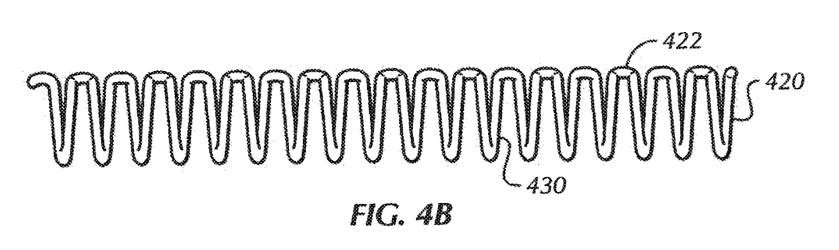
FIG. 4B is a side view of a frame member for use in a suture anchor apparatus in accordance with at least one example of the invention.

Referring to FIGS. 4A and 4B, in some examples, a wire form 430 can be formed into one of the patterns described herein, such as, but not limited to a wavelike pattern, and further formed into a circular shape, when viewed from an end. In some examples, the wire form 430 can include a length longer than is needed within a suture anchor, such as one or more of the suture anchors 200, 300 described herein. In such examples, the wire form 430 can be cut into one or more lengths sufficient to form a frame member 420 for use with a suture anchor. In some examples, the wire form 430 is cut to a length according to a specific number of suture loops 422. For instance, the wire form 430, in some examples, can be cut to include seven suture loops 422, as was included in the example suture anchor 200 described herein, or can be cut to include six suture loops 422, as was included in the example suture anchor 300 described herein. In other examples, the wire form 430 can be cut to form a frame member 420 including more than seven suture loops 422 or fewer than six suture loops 422.

Figure 5A:
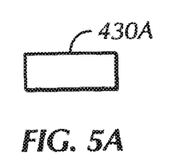
FIGS. 5A-5H are cross-sectional views of various examples of wire for use in a frame member of a suture anchor apparatus in accordance with at least one example of the invention.
Figure 5B:
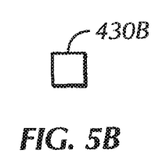
Figure 5C:
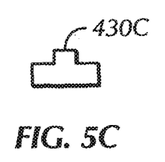
Figure 5D:
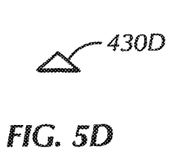
Figure 5E:
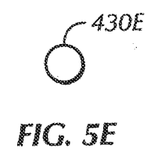
Figure 5F:
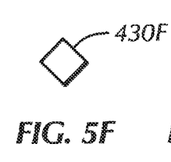
Figure 5G:
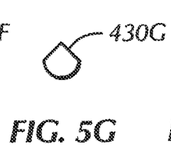
Figure 5H:
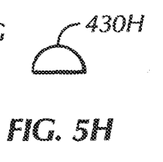

Referring to FIGS. 5A-5H, various examples of cross sections of the wire form 430 are shown. The wire form 430, in some examples, can be drawn, extruded, cut, or otherwise formed into various cross sections. For instance, in various examples, the wire form 430 can include a rectangular cross section (FIG. 5A), a square cross section (FIG. 5B), a T-shaped cross section (FIG. 5C), a triangular cross section (FIG. 5D), a circular cross section (FIG. 5E), a diamond-shaped cross section (FIG. 5F), tear-drop-shaped cross section (FIG. 5G), or a hemispherical cross section (FIG. 5H). It should be understood that, in other examples, the wire form 430 is contemplated as having cross sections other than those shown in FIGS. 5A-5H, such as, but not limited to a cross-shaped cross section, an ovular cross section, an elliptical cross section, a semicircular cross section, a rhomboid cross section, a pentagonal cross section, a hectagonal cross section, or the like. In various examples, the shape of the cross section of the wire form 430 can enhance or facilitate one or more of forming of the wire form 430 into the desired shape for the frame member 420, flexibility of the wire form 430, gripping of the wire frame 430, or the like. For instance, in some examples, a wire form 430 of a particular cross section can be better suited for a suture anchor for use in a particular application than a wire form of another cross section.

The present inventors have recognized various advantages of the subject matter described herein. For instance, in some examples, the suture anchors described herein can be used to anchor a therapy delivery element or other device with respect to a patient without a suture being directly in contact with a sheath of the suture anchor. In this way, the present subject matter can decrease the likelihood of a suture cutting through an exterior of a suture anchor, as can be a problem with other suture anchors. Additionally, in some examples, the suture anchor can include a pre-loaded suture, thereby decreasing the amount of time required to engage the suture anchor by eliminating the need to put the suture in place first before tightening the suture. While various advantages of examples of the example apparatuses, systems, and methods are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description. The drawings show, by way of illustration, specific examples in which the present apparatuses and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. A suture anchor comprising:
   a sheath including a lumen, the lumen being sized to accept a therapy delivery element within the lumen; and
   a frame member disposed at least partially within the sheath, the frame member including at least two suture loops extending from the sheath, the suture loops configured to receive a suture, wherein tightening of the suture causes compression of the frame member to constrict the lumen of the sheath to frictionally engage the therapy delivery element;
   wherein the sheath includes a circumferentially flattened area when the suture anchor is in a relaxed state, wherein the at least two suture loops extend beyond the circumferentially flattened area in a side view, and wherein the at least two suture loops are disposed substantially along a longitudinal line along an outer surface of the sheath.

2. The suture anchor of claim 1, wherein the frame member includes a substantially circular shape when viewed from an end, the frame member being substantially coaxial with the lumen of the sheath.

3. The suture anchor of claim 2, wherein the frame member includes a wave-shaped pattern when flattened, the wave-shaped pattern including peaks, the peaks forming the suture loops with the frame member formed into the substantially circular shape.

4. The suture anchor of claim 1, wherein the frame member includes a wire form.

5. The suture anchor of claim 1, wherein the frame member includes more than two suture loops.

6. The suture anchor of claim 1, wherein at least a portion of the sheath is laminated over the frame member.

7. The suture anchor of claim 1, wherein at least a portion of the sheath is overmolded with the frame member.

8. The suture anchor of claim 1, wherein the sheath includes a first portion and a second portion, wherein the first portion includes a first characteristic and the second portion includes a second characteristic different from the first characteristic.

9. The suture anchor of claim 1, wherein the at least two suture loops flare outwardly from the sheath.

10. A suture anchor comprising:
    a sheath including a first portion and a second portion that partially surrounds the first portion, the first portion and the second portion being formed from different materials, wherein the sheath defines a lumen, the lumen being sized to accept a therapy delivery element within the lumen, the therapy delivery element including a stimulation lead, a pacing or defibrillation lead, a sensing lead, or a fluid delivery conduit; and
    a frame member disposed at least partially within the sheath, the frame member including a wave-shaped pattern when flattened, the frame member including at least two suture loops extending from the sheath, the suture loops formed from peaks of the wave-shaped pattern of the frame member with the frame member formed into a substantially circular shape, the suture loops configured to receive a suture, wherein tightening of the suture causes compression of the frame member to constrict the lumen of the sheath to frictionally engage the therapy delivery element.

11. The suture anchor of claim 10, wherein the frame member includes a wire form.

12. The suture anchor of claim 10, wherein the sheath includes a flattened area, wherein the at least two suture loops extend beyond the flattened area in a side view, and wherein the at least two suture loops are disposed substantially along a longitudinal line along an outer surface of the sheath.

13. The suture anchor of claim 10, wherein at least a portion of the sheath is laminated over the frame member.

14. The suture anchor of claim 10, wherein at least a portion of the sheath is overmolded with the frame member.

15. The suture anchor of claim 10, wherein the first portion includes a first hardness of a first durometer, and the second portion includes a second hardness of a second durometer that is greater than or less than the first durometer.

16. The suture anchor of claim 10, wherein the at least two suture loops flare outwardly from the sheath.

17. The suture anchor of claim 10, wherein the frame member is disposed between the first portion and the second portion.

18. A suture anchor comprising:
    a sheath including a first portion and a second portion that circumferentially surrounds the first portion, the first portion defining a lumen, the lumen being sized to accept a therapy delivery element within the lumen; and
    a frame member disposed at least partially between the first portion and the second portion of the sheath, the frame member including a wave-shaped pattern when flattened, the frame member including at least two suture loops extending from the sheath, the suture loops formed from peaks of the wave-shaped pattern of the frame member with the frame member formed into a substantially circular shape, the suture loops configured to receive a suture, the at least two suture loops extending from the sheath and being disposed substantially along a longitudinal line along an outer surface of the sheath, wherein tightening of the suture causes compression of the frame member to constrict the lumen of the sheath to fictionally engage the therapy delivery element.

19. The suture anchor of claim 18, wherein at least a portion of the sheath is laminated over the frame member or overmolded with the frame member.

20. The suture anchor of claim 18, wherein the first portion and the second portion have different material characteristics selected from the group consisting of: hardness, density, lubriciousness, resilience, elasticity, biocompatibility, and color.

21. The suture anchor of claim 18, wherein the sheath includes a flattened area, and wherein the at least two suture loops flare outwardly from the sheath and extends beyond the flattened area in a side view.

* * * * *